US005646180A

United States Patent [19]
Chaturvedi

[11] Patent Number: 5,646,180
[45] Date of Patent: Jul. 8, 1997

[54] TREATMENT OF THE CNS EFFECTS OF HIV

[75] Inventor: Pravin Ramsewak Chaturvedi, Quincy, Mass.

[73] Assignee: Vertex Pharmaceuticals Incorporated, Cambridge, Mass.

[21] Appl. No.: 567,199

[22] Filed: Dec. 5, 1995

[51] Int. Cl.$^6$ .................................................. A16K 31/34
[52] U.S. Cl. ............................................................ 514/471
[58] Field of Search ............................................. 514/471

[56] References Cited

FOREIGN PATENT DOCUMENTS

WO94/05639  3/1994  WIPO ........................ C07D 215/48

OTHER PUBLICATIONS

M.E. Brewster and N. Bodor, "Redox Approaches to Drug Delivery to the Central Nervous System", in *Bioavailability of Drugs to the Brain and the Blood–Brain Barrier*, J. Frankenhiem and R.M. Brown, eds., Research Monograpph 120, pp. 169–201, U.S. Department of Health and Human Services, U.S. Government Printing Office, Washington, D.C. (1992).

J.–H. Lin, et al., "Physiological Disposition and Metabolism of L–735,524, A Potent HIV Protease Inhibitor in Laboratory Animals", *Pharmaceutical Research.*, 10(10), suppl., p. S–374 (1993).

B.V. Sheety, et al., "Preclinical Pharmacokinetics and Distribution to Tissue of AG1343, an Inhibitor of Human Immunodeficiency Virus Type 1 Protease", *Antimicrob. Agents Chemother.*, 40(1), pp. 110–114 (1996).

WPI abstract No. C94–046567 of WO 94/05639(Bhisetti et al.). 1994.

Medline abstract No. 00115308, Portegies, Drugs (New Zealand) 49 Suppl 1, pp. 25–31. 1995.

Medline abstract No. 00094568, Tozzi et al., AIDS (United States), 7(5) pp. 683–692. 1993.

Medline abstract No. 00121958, Chiesi et al., J. Acquir. Immune Defic. Syndr. Hum. Retrovirol.(United States), 11(1) pp. 39–44. 1995.

Isselbacher et al. "Harrison's Principles of Internal Medicine", vol. 2, published by McGraw–Hill, pp. 1589–1591. 1994.

*Primary Examiner*—Raymond Henley, III
*Attorney, Agent, or Firm*—Fish & Neave; James F. Haley, Jr.; Jeffrey D. Hsi

[57] ABSTRACT

Methods and compositions for treating the central nervous system (CNS) effects of HIV, particularly AIDS related dementia.

2 Claims, No Drawings

TREATMENT OF THE CNS EFFECTS OF HIV

TECHNICAL FIELD OF THE INVENTION

Methods and compositions for treating the central nervous system (CNS) effects of HIV, particularly AIDS related dementia.

BACKGROUND OF THE INVENTION

The human immunodeficiency virus ("HIV") is the causative agent for acquired immunodeficiency syndrome ("AIDS")—a disease characterized by the destruction of the immune system, particularly of $CD4^+$ T-cells, with attendant susceptibility to opportunistic infections—and its precursor AIDS-related complex ("ARC")—a syndrome characterized by symptoms such as persistent generalized lymphadenopathy, fever and weight loss.

As in the case of several other retroviruses, HIV encodes the production of a protease which carries out post-translational cleavage of precursor polypeptides in a process necessary for the formation of infectious virions (S. Crawford et al., "A Deletion Mutation in the 5' Part of the pol Gene of Moloney Murine Leukemia Virus Blocks Proteolytic Processing of the gag and pol Polyproteins", *J. Virol.*, 53, p. 899 (1985)). These gene products include pol, which encodes the virion RNA-dependent DNA polymerase (reverse transcriptase), an endonuclease, HIV protease, (reverse transcriptase), an endonuclease, HIV protease, and ga, which encodes the core-proteins of the virion (H. Toh et al., "Close Structural Resemblance Between Putative Polymerase of a Drosophila Transposable Genetic Element 17.6 and pol gene product of Moloney Murine Leukemia Virus", *EMBO J.*, 4, p. 1267 (1985); L. H. Pearl et al., "A Structural Model for the Retroviral Proteases", Nature, pp. 329–351 (1987); M. D. Power et al., "Nucleotide Sequence of SRV-1, a Type D Simian Acquired Immune Deficiency Syndrome Retrovirus", Science, 231, p. 1567 (1986)).

A number of synthetic anti-viral agents have been designed to target various stages in the replication cycle of HIV. These agents include compounds which block viral binding to $CD4^+$ T-lymphocytes (for example, soluble CD4), and compounds which interfere with viral replication by inhibiting viral reverse transcriptase (for example, didanosine and zidovudine (AZT)) and inhibit integration of vital DNA into cellular DNA (M. S. Hirsh and R. T. D'Aqulia, "Therapy for Human Immunodeficiency Virus Infection", *N. Eng. J. Med.*, 328, p. 1686 (1993)). However, such agents, which are directed primarily to early stages of viral replication, do not prevent the production of infectious virions in chronically infected cells. Furthermore, administration of some of these agents in effective amounts has led to cell-toxicity and unwanted side effects, such as anemia and bone marrow suppression.

More recently, the focus of anti-viral drug design has been to create compounds which inhibit the formation of infectious virions by interfering with the processing of viral polyprotein precursors. Processing of these precursor proteins requires the action of virus-encoded proteases which are essential for replication (Kohl, N. E. et al. "Active HIV Protease is Required for Viral Infectivity" *Proc. Natl. Acad. Sci. USA*, 85, p. 4686 (1988)). The anti-viral potential of HIV protease inhibition has been demonstrated using peptidal inhibitors. Such peptidal compounds, however, are typically large and complex molecules that tend to exhibit poor bioavailability and are not generally consistent with oral administration. Accordingly, the need still exists for compounds that can effectively inhibit the action of viral proteases, for use as agents for preventing and treating chronic and acute vital infections.

AIDS and other HIV related diseases often have CNS components. One such component is AIDS related dementia.

While there are a growing number of treatments for HIV and its related diseases, e.g., AIDS and ARC, such treatments have had little or no effect on the CNS effects of HIV infection.

The reason that these treatments are not as effective against the CNS effects of HIV is that the pharmaceutical compositions that characterize them are not able to cross the blood brain barrier in an amount sufficient to the effect and slow HIV infection in the CNS.

AZT, the most well-known of the HIV treatments, for example, has a brain/blood distribution of only about 0.3. And after 60 minutes, no AZT is found in brain tissue. The other HIV nucleosides, ddC, DDI and d4T, have even worse distribution profiles in the CNS.

HIV protease inhibitors also do not penetrate to the CNS at useful levels. Abbott's ABT 538, for example, displays very limited CNS penetration. Searle's inhibitor has a brain/blood distribution of 0.2 to 0.3. Merck's L-535524 has about the same distribution.

Thus, the present HIV nucleoside and protease based therapies have less than desired effects on the CNS components of HIV.

SUMMARY OF THE INVENTION

This invention provides a method and a composition for treating the CNS components of HIV, particularly AIDS related dementia.

The method and composition of this invention are characterized by an HIV protease inhibitor of Formula I:

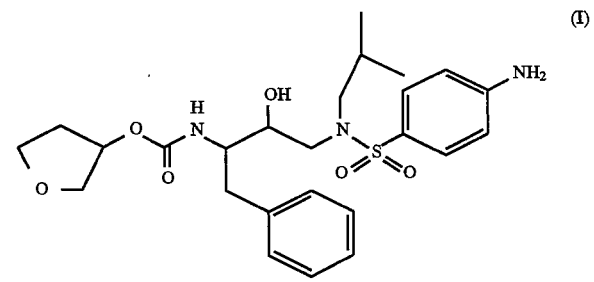

(I)

DETAILED DESCRIPTION OF THE INVENTION

The compound of Formula I is an HIV protease inhibitor. However, unlike other protease inhibitors, it has a brain/blood distribution of more than 1.0. This means that it is very effective in crossing the blood/brain barrier. In fact, it is present in the brain at about the same level as it is present in the blood. In addition, the compound of Formula I has an unexpectedly long half life in the brain. Both of these properties result in the compound of Formula I being unexpectedly useful in treating the CNS effects of HIV, particularly AIDS related dementia.

The compound of Formula I can be made from available starting materials using any one of several well known synthetic routes. Examples of such syntheses include those described in International Patent Application WO 94/05639, which is hereby incorporated by reference.

In general, sulfonamides of formula I are conveniently obtained from α-amino acid derivatives having the general formula P-N(G)-CH(D)-COOH, wherein P is defined as THF-O-C(O)— or an amino acid protecting group, D is defined as benzyl, and G is H or benzyl. Suitable amino acid protecting groups are described in numerous references, including T. W. Greene and P. G. M. Wuts, *Protective Groups in Organic Synthesis*, 2d Ed., John Wiley and Sons (1991). Examples of such amino acid protecting groups include, but are not limited to, carbamate containing groups such as Boc, Cbz or Alloc, or alternatively, the amine may be protected as an alkyl derivative such as N,N-dibenzyl or trityl. Such α-amino acid derivatives are often commercially available or may be conveniently prepared from commercially available α-amino acid derivatives using known techniques. Although this invention envisions the use of racemic mixtures of such starting materials, a single enantiomer in the S configuration is preferred.

Using known techniques, the α-amino acid derivative of general formula P-N(G)-CH(D)-COOH may be readily converted to an amino ketone derivative of general formula P-N(G)-CH(D)-CO-CH$_2$-X, wherein X is a leaving group which suitably activates the α-carbon (i.e., increases the susceptibility of the methylene to nucleophilic attack). Suitable leaving groups are well known in the art and include halides and sulfonates, such as methanesulfonate, trifluoromethanesulfonate or 4-toluenesulfonate. X may also be a hydroxyl which is converted in situ to a leaving group (e.g. by treatment with a trialkyl- or triarylphosphine in the presence of a dialkylazodicarboxylate). Methods for the formation of such amino ketone derivatives also are well known to those of skill in the art (see, for example, S. J. Fittkau, *J. Prakt. Chem.*, 315, p. 1037 (1973)). Alternatively, certain amino ketone derivatives are commercially available (e.g., from Bachem Biosciences, Inc., Philadelphia, Pa.).

The amino ketone derivative may then be reduced to the corresponding amino alcohol, represented by the formula P-N(G)-CH(D)-CH(OH)-CH$_2$-X. Alternatively, the amino ketone derivative can be reduced later in the synthetic scheme. Many techniques for reduction of amino ketone derivatives such as P-N(G)-CH(D)-CO-CH$_2$-X are well known to those of ordinary skill in the art (Larock, R. C. "Comprehensive Organic Transformations", pp. 527–547, VCH Publishers, Inc.© 1989 and references cited therein). A preferred reducing agent is sodium borohydride. The reduction reaction is conducted at a temperature of from about −40° C. to about 40° C. (preferably, at about −10° C. to about 20° C.), in a suitable solvent system such as, for example, aqueous or neat tetrahydrofuran or a lower alcohol, such as methanol or ethanol. Although this invention envisions both stereospecific and non-stereospecific reduction of the amino ketone derivative P-N(G)-CH(D)-CO-CH$_2$-X, stereoselective reduction is preferred. Stereoselective reduction may be accomplished by use of chiral reagents known in the art. In the present invention, stereoselective reduction may be conveniently achieved, for instance, under non-chelating reducing conditions, where chiral induction of the newly formed hydroxyl group is set by the stereochemistry of the D group (i.e., Felkin-Ahn addition of hydride). We particularly prefer stereoselective reductions wherein the resulting hydroxyl is syn to D. We have found that when the hydroxyl group is syn to D, the final sulfonamide product is an HIV protease inhibitor of higher potency than the anti diastereomer.

The hydroxyl group of the amino alcohol may optionally be protected by any known oxygen protecting group (such as trialkylsilyl, benzyl, or alkyloxymethyl) to yield a protected amino alcohol having the formula P-N(G)-CH(D)-C(OR$^7$)-CH$_2$-X, wherein R$^7$ is H or any suitable hydroxy protecting group. Several useful protecting groups are described in T. W. Greene and P. G. M. Wuts, *Protective Groups in Organic Synthesis*, 2d Ed., John Wiley and Sons (1991).

This protected amino alcohol may then be reacted with a nucleophilic amine compound to form an intermediate of formula III:

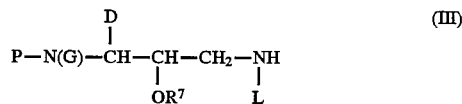

wherein P is defined as THF-O-C(O)- or an amino acid protecting group, D is benzyl, R$^7$ is as described above, and L is either isobutyl or hydrogen.

Alternatively, an appropriately protected and activated amino acid derivative may be reacted with a nucleophilic nitro compound (e.g., a nitromethane anion or a derivative thereof), which after coupling, can be reduced to yield an intermediate of formula III.

In a particularly advantageous synthetic scheme, simultaneous activation of the methylene and protection of the alcohol may be accomplished by forming an N-protected amino epoxide from the oxygen and its adjacent methylene to give an intermediate of formula II:

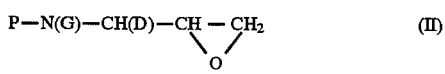

wherein P, D and G are defined above. Suitable solvent systems for preparing the N-protected amino epoxide include anhydrous or aqueous organic solvents such as ethanol, methanol, isopropanol, tetrahydrofuran, dioxane, dimethylformamide and the like (including mixtures thereof). Suitable bases for producing the epoxide include alkali metal hydroxides, potassium t-butoxide, DBU and the like. A preferred base is potassium hydroxide.

Preferably, the compound of Formula I is made by preparing the N-protected amino epoxide by reacting the dianion of an acetic acid derivative containing a potential leaving group on the α-carbon with a cyclic N-carboxyanhydride of a protected α-amino acid (such as BOC-Phe-NCA, available from Propeptide) or other appropriately protected and activated amino acid derivative. This method incorporates the use of haloacetic acids or, generally, heteroatom-substituted acetic acids wherein the heteroatom may be converted to a leaving group. A preferred acetic acid dianion is (methylthio)acetic acid dianion. The resulting amino ketone may then be reduced (e.g., with sodium borohydride). In the case where the nucleophile is the dianion of methylthioacetic acid, the resulting amino alcohol is readily converted to the amino epoxide by alkylation (e.g., with methyl iodide) followed by ring closure (using, for example, sodium hydride).

Reaction of the N-protected amino epoxide (or other suitably activated intermediate) with an amine is carried out neat, i.e. in the absence of solvent, or in the presence of a polar solvent such as lower alkanols, water, dimethylformamide or dimethylsulfoxide. The reaction can be carried out conveniently between about −30° C. and 120° C., preferably between about −5° C. and 100° C. Alternatively, the reaction may be carried out in the presence of an activating agent, such as activated alumina in an inert solvent, preferably an ether, such as diethyl ether, tetrahydrofuran, dioxane, or tert-butyl methyl ether, conveniently from about room temperature to about 110° C., as described by Posner and Rogers, *J. Am Chem. Soc.*, 99, p. 8208 (1977). Other activating reagents include lower trialkyl-aluminum species, such as triethylaluminum, or dialkylaluminum halide species, such as diethylaluminum chloride (Overman and Flippin, *Tetrahedron Letters*, p. 195 (1981)). Reactions involving these species are conveniently carried out in inert solvents such as dichloromethane, 1,2-dichloroethane, toluene, or acetonitrile between about 0° C. and about 110° C. Further methods of displacing leaving groups, or opening epoxides with amines or their equivalents such as azides or trimethylsilyl cyanide (Gassman and Guggenheim, *J. Am. Chem. Soc.* 104, p. 5849 (1982)), are known and will be apparent to those of ordinary skill in the art.

Compounds of formulae II and III, and functionality-protected derivatives thereof, are useful as intermediates for the preparation of the compound of formula I. Where L represents isobutyl, compounds of formula III may be converted to the compound of formula I by reaction with sulfonyl-activated species to form the sulfonamide. Methods for preparing such sulfonyl-activated species are well within the ordinary skill of the art. Typically, sulfonyl halides are used to obtain sulfonamides. Many sulfonyl halides are commercially available; others may be easily obtained using conventional synthetic techniques (Gilbert, E. E. "Recent Developments in Preparative Sulfonation and Sulfation" *Synthesis* 1969:3 (1969) and references cited therein; Hoffman, R. V. "M-Trifluoromethylbenzenesulfonyl Chloride" *Org. Synth. Coll. Vol. VII*, John Wiley and Sons (1990); Hartman, G. D. et. al. "4-Substituted Thiophene-and Furan-2-sulfonamides as Topical Carbonic Anhydrase Inhibitors" *J. Med. Chem.*, 35, p. 3822 (1992) and references cited therein.

In the case of compounds of formula III wherein L is hydrogen, conversion of the resultant primary amine to a secondary amine may be carried out by known techniques. Such techniques include reaction with an alkyl halide or alkyl sulfonate, or by reductive alkylation with an aldehyde using, for instance, catalytic hydrogenation or sodium cyanoborohydride (Borch et al., *J. Am. Chem. Soc.*, 93, p. 2897 (1971)). Alternatively, the primary amine may be acylated followed by reduction with borane or another suitable reducing reagent, for example, as described by Cushman et al., *J. Org. Chem.*, 56, p. 4161 (1991). This technique is especially useful in compounds of formula III where P represents a protecting group such as tert-butoxycarbonyl (Boc) or benzyloxycarbonyl (Cbz) and G is hydrogen, or where P and G are both benzyl.

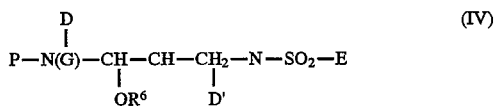

(IV)

If variables P and G of a particular compound of formula IV represent removable protecting groups, removal of either or both groups followed by reaction of the resulting amine with an appropriate activated reagent will advantageously yield a different compound of formula IV. For instance, carbamates may be obtained by reaction with chlorocarbonates or with carbonates esterified with leaving groups such as 1-hydroxybenzotriazole (HOBT) or HOSu, or 4-nitrophenol (protonated species). An example of such a carbonate is N-succinimidyl-(3S)-tetrahydrofuran-3-yl carbonate. It will be readily recognized that in order to facilitate specific reactions, the protection of one or more potentially reactive groups followed by subsequent removal of that group may be required. Such modification to the reaction schemes outlined above are within the ordinary skill of the art.

As can be appreciated by the skilled artisan, the above synthetic schemes are not intended to comprise a comprehensive list of all means by which the compounds described and claimed in this application may be synthesized. Further methods will be evident to those of ordinary skill in the art.

The compound of this invention may be modified by appending appropriate functionalites to enhance selective biological properties. Such modifications are known in the art and include those which increase biological penetration into a given biological compartment (e.g., blood, lymphatic system, central nervous system), increase oral availability, increase solubility to allow administration by injection, alter metabolism and alter rate of excretion.

The compound of the present invention is an excellent ligand for aspartyl proteases, particularly HIV-1 and HIV-2 proteases. Accordingly, the compound is capable of targeting and inhibiting late stage events in HIV replication, i.e., the processing of the viral polyproteins by HIV encoded proteases. The compound inhibits the proteolytic processing of viral polyprotein precursors by inhibiting aspartyl protease. Because aspartyl protease is essential for the production of mature virions, inhibition of that processing effectively blocks the spread of virus by inhibiting the production of infectious virions, particularly from chronically infected cells. The compound according to this invention advantageously inhibits the ability of the HIV-1 virus to infect immortalized human T cells over a period of days, as determined by an assay of extracellular p24 antigen—a specific marker of viral replication. Other anti-viral assays have confirmed the potency of this compound.

The compound of this invention may be employed in a conventional manner for the treatment of viruses, such as HIV and HTLV, which depend on aspartyl proteases for obligatory events in their life cycle. Such methods of treatment, their dosage levels and requirements may be selected by those of ordinary skill in the art from available methods and techniques. For example, the compound of this invention may be combined with a pharmaceutically acceptable adjuvant for administration to a virally-infected patient in a pharmaceutically acceptable manner and in an amount effective to lessen the severity of the viral infection or to alleviate pathological effects associated with HIV infection.

Alternatively, the compound of this invention may be used in prophylactics and methods for protecting individuals against viral infection during a specific event, such as childbirth, or over an extended period of time. The compound may be employed in such prophylactics either alone or together with other antiretroviral agents to enhance the efficacy of each agent. As such, the novel protease inhibitors of this invention can be administered as agents for treating or preventing HIV infection in a mammal.

The compound of formula I may be readily absorbed into the bloodstream of mammals upon oral administration. The compound of formula I having a molecular weight of less than about 600 g/mole and aqueous solubility of greater than or equal to 0.1 mg/mL is likely to demonstrate high and consistent oral availability. This surprisingly impressive oral availability makes the compound an excellent agent for orally-administered treatment and prevention regimens against HIV infection.

In addition to being orally bioavailable, the compound of this invention also has an impressively high therapeutic index (which measures toxicity versus anti-viral effect). Accordingly, the compound of this invention is effective at lower dosage levels than many previously described conventional antiretroviral agents and avoid many of the severe toxic effects associated with those drugs. The potential of this compound to be delivered at doses far exceeding its effective antiviral level is advantageous in slowing or preventing the possibility of resistant variants developing.

The compound of this invention may be administered to a healthy or HIV-infected patient either as a single agent or in combination with other anti-vital agents which interfere with the replication cycle of HIV. By administering the compound of this invention with other anti-vital agents which target different events in the vital life cycle, the therapeutic effect of these compounds is potentiated. For instance, the co-administered anti-vital agent can be one which targets early events in the life cycle of the virus, such as cell entry, reverse transcription and viral DNA integration into cellular DNA. Anti-HIV agents targeting such early life cycle events include, didanosine (ddI), dideoxycytidine (ddC), d4T, zidovudine (AZT), 3TC, 935U83, 1592U89, 524W91, polysulfated polysaccharides, sT4 (soluble CD4), ganiclovir, trisodium phosphonoformate, eflornithine, ribavirin, acyclovir, alpha interferon and tri-menotrexate. Additionally, non-nucleoside inhibitors of reverse transcriptase, such as TIBO, delavirdine (U90) or nevirapine, may be used to potentiate the effect of the compounds of this invention, as may viral uncoating inhibitors, inhibitors of trans-activating proteins such as tat or rev, or inhibitors of the viral integrase.

Combination therapies according to this invention exert an additive or synergistic effect in inhibiting HIV replication because each component agent of the combination acts on a different site of HIV replication. The use of such combination therapies also advantageously reduces the dosage of a given conventional anti-retroviral agent which would be required for a desired therapeutic or prophylactic effect, as compared to when that agent is administered as a monotherapy. Such combinations may reduce or eliminate the side effects of conventional single anti-retroviral agent therapies, while not interfering with the anti-retroviral activity of those agents. These combinations reduce potential of resistance to single agent therapies, while minimizing any associated toxicity. These combinations may also increase the efficacy of the conventional agent without increasing the associated toxicity. In particular, we have discovered that in combination with other anti-HIV agents, the compound of this invention acts in an additive or synergistical manner in preventing the replication of HIV in human T cells. Preferred combination therapies include the administration of the compound of this invention with AZT, ddI, ddC, d4T, 3TC, 935U83, 1592U89, 524W91 or a combination thereof.

Alternatively, the compound of this invention may also be co-administered with other HIV protease inhibitors such as saquinavir (Ro 31-8959, Roche), L-735,524 (Merck), ABT 538 (A-80538, Abbott), AG 1341 (Agouron), XM 412 (DuPont Merck), XM 450 (DuPont Merck), BMS 186318 (Bristol-Meyers Squibb) and CPG 53,437 (Ciba Geigy) or prodrugs of these or related compounds to increase the effect of therapy or prophylaxis against various viral mutants or members of HIV quasi species.

We prefer administering the compound of this invention as a single agent or in combination with retroviral reverse transcriptase inhibitors, such as derivatives of AZT, or other HIV aspartyl protease inhibitors, including multiple combinations comprising from 3–5 agents. We believe that the co-administration of the compound of this invention with retroviral reverse transcriptase inhibitors or HIV aspartyl protease inhibitors may exert a substantial additive or synergistic effect, thereby preventing, substantially reducing, or completely eliminating vital replication or infection or both, and symptoms associated therewith.

The compound of this invention can also be administered in combination with immunomodulators and immunostimulators (e.g., bropirimine, anti-human alpha interferon antibody, IL-2, GM-CSF, interferon alpha, diethyldithiocarbamate, tumor necrosis factor, naltrexone, tuscarasol, and rEPO); and antibiotics (e.g., pentamidine isethiorate) to prevent or combat infection and disease associated with HIV infections, such as AIDS and ARC.

When the compound of this invention is administered in combination therapies with other agents, they may be administered sequentially or concurrently to the patient. Alternatively, pharmaceutical compositions according to this invention may comprise a combination of an aspartyl protease inhibitor of this invention and another therapeutic or prophylactic agent.

Although this invention focuses on the use of the compound disclosed herein for preventing and treating HIV infection, the compound of this invention can also be used as an inhibitory agent for other viruses which depend on similar aspartyl proteases for obligatory events in their life cycle. These viruses include other AIDS-like diseases caused by retroviruses, such as simian immunodeficiency viruses, HTLV-I and HTLV-II. In addition, the compound of this invention may also be used to inhibit other aspartyl proteases, and in particular, other human aspartyl proteases, including renin and aspartyl proteases that process endothelin precursors.

The compositions of this invention are typically taken orally. They contain an amount of the compound of Formula I that is effective in inhibiting the replication of HIV by inhibiting its HIV protease in the CNS.

The compound of Formula I is employed in the method and composition of this invention in combination with a pharmaceutically acceptable carrier. Typically, it is also used in combination with other AIDS therapies, particularly AZT and 3TC.

Pharmaceutical compositions of this invention comprise the compound of the present invention, and pharmaceutically acceptable salts thereof, with any pharmaceutically acceptable carrier, adjuvant or vehicle. Pharmaceutically acceptable carriers, adjuvants and vehicles that may be used in the pharmaceutical compositions of this invention include, but are not limited to, ion exchangers, alumina, aluminum stearate, lecithin, self-emulsifying drug delivery systems (SEDDS) such as dα-tocopherol polyethyleneglycol 1000 succinate, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and γ-cyclodextrin, or chemically modified derivatives such as hydroxyalkylcyclodextrins, including 2- and 3-hydroxypropyl-β-cyclodextrins, or other solubilized derivatives may also be advantageously used to enhance delivery of the compound of formula I.

The pharmaceutical compositions of this invention may be administered orally, parenterally, by inhalation spray, topically, rectally, nasally, buccally, vaginally or via an implanted reservoir. We prefer oral administration or administration by injection. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intrasynovial, intrasternal, intrathecal, intralesional and intracranial injection or infusion techniques.

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant such as Ph. Helv or a similar alcohol.

The pharmaceutical compositions of this invention may be orally administered in any orally acceptable dosage form including, but not limited to, capsules, tablets, and aqueous suspensions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are administered orally, the active ingredient is combined with emulsifying and suspending agents. If desired, certain sweetening and/or flavoring and/or coloring agents may be added.

The pharmaceutical compositions of this invention may also be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

Topical administration of the pharmaceutical compositions of this invention is especially useful when the desired treatment involves areas or organs readily accessible by topical application. For application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax and water. Alternatively, the pharmaceutical composition can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical compositions of this invention may also be topically applied to the lower intestinal tract by rectal suppository formulation or in a suitable enema formulation. Topically-transdermal patches are also included in this invention.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

Dosage levels of between about 0.01 and about 100 mg/kg body weight per day, preferably between about 0.5 and about 75 mg/kg body weight per day of the active ingredient compound are useful in the prevention and treatment of viral infection, including HIV infection. Typically, the pharmaceutical compositions of this invention will be administered from about 1 to about 5 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Preferably, such preparations contain from about 20% to about 80% active compound.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level, treatment should cease. Patients may, however, require intermittent treatment on a long-term basis upon any recurrence of disease symptoms.

As the skilled artisan will appreciate, lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the infection, the patient's disposition to the infection and the judgment of the treating physician.

In order that this invention be more fully understood, the following examples are set forth. These examples are for the purpose of illustration only and are not to be construed as limiting the scope of the invention in any way.

EXAMPLE 1

Precursor A. A solution of 102 mg of N-( (2 syn, 3S )-2-hydroxy-4-phenyl-3-((S)-tetrahydro furan-3-yloxycarbonylaminobutylamine in 4:1 $CH_2Cl_2$/saturated aqueous $NaHCO_3$ was treated sequentially, at ambient temperature under an atmosphere of nitrogen, with 65 mg of p-nitrobenzenesulfonyl chloride and 51 mg of sodium bicarbonate. The mixture was stirred for 14 h, diluted with $CH_2Cl_2$, washed with saturated NaCl, then dried over $MgSO_4$, filtered, and concentrated in vacuo. The residue was purified by low pressure silica gel chromatography using 20% diethyl ether/$CH_2Cl_2$ as eluent to provide 124 mg of the title product as a white solid. TLC: Rf=0.36, 20% diethyl ether/$CH_2Cl_2$. HPLC: Rt=15.15 min. ($^1$H)-NMR ($CDCl_3$) consistent with structure.

EXAMPLE 2

Compound I. A solution of 124 mg of the resultant compound of Example 1 in ethyl acetate was treated, at ambient temperature, with 13 mg of 10% palladium on carbon. The mixture was stirred for 14 h under an atmosphere of hydrogen, filtered through a pad of Celite filter agent, and concentrated in vacuo. The residue was subjected to preparative HPLC to yield 82 mg of the title product as a white solid. TLC: Rf=0.10, 20% ether/CH$_2$Cl$_2$. HPLC: Rt=13.16 min. ($^1$H)-NMR (CDCl$_3$) consistent with structure.

While we have described a number of embodiments of this invention, it is apparent that our basic constructions may be altered to provide other embodiments which utilize the products and methods of this invention. Therefore, it will be appreciated that the scope of this invention is to be defined by the appended claims, rather than by the specific embodiments which have been presented by way of example.

I claim:

1. A method for treating the CNS effects of HIV comprising the step of administering to a patient a pharmaceutical composition comprising a compound of Formula I:

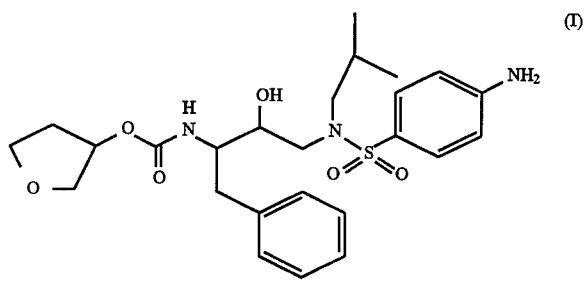

in an amount effective to inhibit HIV in the CNS.

2. The method according to claim 1, wherein the composition further comprises AZT, 3TC or both.

* * * * *

UNITED STATES PATENT AND TRADEMARK OFFICE
CERTIFICATE OF CORRECTION

PATENT NO. : 5,646,180
DATED : July 8, 1997
INVENTOR(S) : Pravin Ramsewak Chaturvedi It is certified that error appears in the above-identified patent and that said Letters Patent is hereby corrected as shown below:

Title page,
Item [56], References Cited, under OTHER PUBLICATIONS, replace "Monograpph" with -- Monograph --.

Column 1,
Line 29, replace "ga," with -- gag, --.
Line 45, replace "vital" with -- viral --.

Column 6,
Line 4, replace "functionalites" with -- functionalities --.
Line 17, replace "vital" with -- viral --.

Column 7,
Lines 3, 5 and 8, replace "anti-vital" with -- anti-viral --.
Line 6, replace "vital" with -- viral --.

Column 10,
Line 51, replace "tetrahydro furan" with -- tetrahydrofuran --.

Signed and Sealed this

Twenty-first Day of May, 2002

*Attest:*

*Attesting Officer*

JAMES E. ROGAN
*Director of the United States Patent and Trademark Office*